United States Patent
Meijs et al.

[11] Patent Number: 5,994,133
[45] Date of Patent: Nov. 30, 1999

[54] CELL GROWTH SUBSTRATE POLYMER

[75] Inventors: Gordon Francis Meijs, Murrumbena; Bronwyn Glenice Laycock, Heidelberg Heights; Madeleine Clare Griffiths, Hornsby, all of Australia; Edith Cheong, Pulan Pinang, Malaysia; John Gerard Steele, North Rocks; Graham Johnson, Peakhurst, both of Australia

[73] Assignees: Novartis AG, Basel, Switzerland; Commonwealth Scientific and Industrial Research Organisation, Campbell, Australia

[21] Appl. No.: 08/793,204

[22] PCT Filed: Mar. 27, 1996

[86] PCT No.: PCT/EP96/01340

§ 371 Date: Jan. 6, 1998

§ 102(e) Date: Jan. 6, 1998

[87] PCT Pub. No.: WO96/31548

PCT Pub. Date: Oct. 10, 1996

[30] Foreign Application Priority Data

Apr. 4, 1995 [AU] Australia ................. PN2160
May 17, 1995 [AU] Australia ................. PN3025

[51] Int. Cl.$^6$ ................. C12N 5/00; C12N 5/02
[52] U.S. Cl. ................. 435/395; 526/72
[58] Field of Search ................. 435/395; 526/246, 526/247, 248, 320, 72

[56] References Cited

U.S. PATENT DOCUMENTS

| 4,440,918 | 4/1984 | Rice et al. | 526/246 |
| 4,818,801 | 4/1989 | Rice et al. | 526/246 |

FOREIGN PATENT DOCUMENTS

| 0084406A1 | 1/1983 | European Pat. Off. . |
| 0330618A2 | 2/1989 | European Pat. Off. . |
| 0335664A2 | 3/1989 | European Pat. Off. . |
| 0379462A2 | 1/1990 | European Pat. Off. . |
| WO9415980 | 12/1993 | WIPO . |

*Primary Examiner*—Avis M. Davenport
*Attorney, Agent, or Firm*—Michael U. Lee

[57] ABSTRACT

Cell growth substrate polymers are described which comprise a macromonomer of the formula (I): $Q\text{-}(PFPE\text{-}L)_{n-1}\text{-}PFPE\text{-}Q$, wherein n is at least 1.0; each PFPE may be the same or different and is a perfluorinated polyether of the formula (II): $-OCH_2CF_2O(CF_2CF_2O)_x(CF_2O)_y CF_2CH_2O-$, wherein the $CF_2CF_2O$ and $CF_2O$ units may be randomly distributed or distributed as blocks throughout the chain and wherein x and y may be the same or different such that the molecular weight of the perfluoropolyether is in the range of from 242 to 4000, L is a difunctional linking group; and Q at each end of the macromonomer is the same or different and is a polymerizable group. The cell growth substrate polymers may be used in the production of corneal implants.

24 Claims, No Drawings

CELL GROWTH SUBSTRATE POLYMER

The invention relates to biocompatible polymers and products formed therefrom, in particular to cell growth materials and implants formed therefrom. There is extensive teaching in the literature about the interaction of tissue cells with the surfaces of synthetic polymer materials that are intended for use in implants. Much of this teaching arises from research that has aimed to design polymer surfaces that would support the very tight and effective attachment of tissue cells to the polymeric surface. Such polymer surfaces are intended for certain demanding implant applications, such as the tissue-contacting surfaces of percutaneous access devices. Another such application would be for use as the lumenal surface of small diameter vascular grafts, where it is intended that endothelial cells would cover the polymer surface. In these applications, tight binding of the cells to the surface of the synthetic polymer is required for the implant to be effective.

In these previous studies, it has been demonstrated that tissue cells such as endothelial cells and fibroblasts do not adhere effectively to the surface of hydrophobic polymers (for example, polymer surfaces with a sessile air-water contact angle of approximately 90 degrees or higher). There is extensive prior teaching that for effective initial attachment of tissue cells to occur, the surface of a hydrophobic polymer needs to be chemically modified to be somewhat wettable (for example, having a sessile air-water contact angle in the range of 80 to 40 degrees).The biochemical mechanism of the initial attachment of tissue cells to such "wettable" polymers has also been the subject of study, and cell attachment has been shown to be dependent upon the adsorption onto the polymer surface of glycoproteins that contain cell-attachment sites. Such glycoproteins include fibronectin, which is found in serum and the extracellular matrix of tissue, and vitronectin, which is found in serum. The prior art therefore teaches that for the effective attachment of tissue cells to a synthetic polymer surface, that polymer would have a surface chemistry that is "wettable" and would effectively adsorb certain glycoproteins to which the tissue cells may bind. In other implant applications such as implants to be placed into connective tissue, where the cell density is low and tight binding of cells may not be required for the implant to be effective, hydrophobic polymers may be acceptable. For certain implants, such as intraocular lenses, or replacement bladders, cell attachment is clearly disadvantageous.

It has generally been thought that the adhesion of cells to synthetic hydrophobic polymeric substrates requires the surface chemistry or topography of the synthetic polymer to be specifically modified to facilitate the adhesion and growth of cells. Glow discharge, plasma polymerization and radiation grafting are a few of the techniques known in the art for such polymer modification. It has also been described that cell attachment to surfaces of synthetic hydrophobic polymers can alternatively be stimulated by the absorption or covalent attachment onto the polymer surface of one or more cell adhesive molecules or fragments thereof, such as fibronectin, vitronectin, collagen, or the like.

Until now the practice in the implantation of artificial corneas for replacement of corneal tissue (that is, stromal tissue) has involved the surgical technique of making an incision above the cornea then cutting a deep pocket behind the epithelial layer to remove the damaged cornea; the replacement cornea was slid into this pocket and the incision closed by suturing. In this case cell growth on the implant was not required, nor necessarily desirable. A recently proposed procedure for the correction of refractive errors is the implantation of a lens within the corneal epithelium. The implantation of such an intraepithelial lens would typically be conducted by removing the corneal epithelial cell layers of the cornea by scraping, then placing the synthetic lens directly onto and in intimate contact with the corneal tissue. The synthetic lens will be held in place during the period immediately after its placement by:

(i) the material characteristics of the synthetic lens allowing it to adhere to the underlying tissue, or (ii) by use of a biocompatible glue, or (iii) by suturing.

For such an intraepithelial implant to be effective, it is critical that the surface and design of the implant be supportive of both the initial coverage of the anterior surface of the lens by corneal epithelial tissue, and the subsequent persistent and effective adhesion of this epithelial tissue. Whereas an intrastromal implant would not be expected to require tight cell adhesion an intraepithelial implant would require tight and comprehensive coverage with corneal epithelial cells and tissue so that the normal functions of the corneal epithelium of forming a barrier to the external environment and providing a substratum for the tear film can occur. From the prior art it would be expected that to satisfy this requirement hydro-phobic polymers will require either chemical surface modification to generate a wettable surface, or else treatment with a glycoprotein that promotes attachment of cells, or a fragment thereof.

U.S. Pat. Nos. 4,440,918 and 4,818,801 describe the use of telechelic perfluorinated polyether monomers and compositions for making contact lenses and other ophthalmic devices with improved oxygen permeability and fouling resistance. U.S. Pat. No. 4,440,918 and U.S. Pat. No. 4,818,801 are principally directed to contact lenses, where deposition of proteins or other bodily constituents results in impaired vision, and where cell growth would be considered detrimental to the use of the telechelic perfluorinated polyethers as contact lenses or other ophthalmic devices, such as intraocular lenses. These materials have also been proposed for other uses such as corneal implants inserted into the eye for the correction of vision difficulties. Such implants known at the time included intraocular lenses and the insertion of a lens into the corneal stroma, particularly in the posterior portion of the corneal stroma. In such cases, the biocompatibility of the polymer would be dependent upon the permeability of the implant to nutrients and small molecular weight molecules and the implant being resistant to fouling. In the case of an intrastromal implant, tight cell adhesion is not expected nor known to be required for the implant to be effective.

Currently available biocompatible polymers for use as cell growth substrates have a number of disadvantages, such as fouling with proteinaceous, carbohydrate and other such materials, poor biostability such that the polymer breaks down when used in the implant situation, and expense associated with additional processing steps such as surface modification to enable the synthetic polymer to support the adhesion and growth of cells since, human cells generally show little tendency to grow evenly on the surface of articles made from polymeric materials.

We have now found that telechelic perfluorinated polyether polymers facilitate the adhesion and growth of cells without the need for additional processing steps. Such polymers are particularly suitable for use as corneal implants of the type which require epithelization. Accordingly, there is provided a cell growth substrate polymer comprising a polymerized macromonomer of the formula I:

$$Q\text{-}(PFPE\text{-}L)_{n-1}\text{-}PFPE\text{-}Q \qquad (I)$$

wherein n is at least 1.0;

each PFPE may be the same or different and is a perfluorinated polyether of formula II:

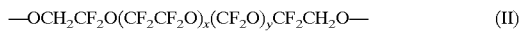
$$\text{—}OCH_2CF_2O(CF_2CF_2O)_x(CF_2O)_yCF_2CH_2O\text{—} \qquad (II)$$

wherein the $CF_2CF_2O$ and $CF_2O$ units may be randomly distributed or distributed as blocks throughout the chain and wherein x and y may be the same or different such that the molecular weight of the perfluoropolyether is in the range of from 242 to 4,000;

L is a difunctional linking group; and

Q at each end of the macromonomer is the same or different and is a polymerizable group.

Preferably n is in the range of from 1 to 5, more preferably in the range of from 1 to 4.

Q is a polymerizable group which preferably contains an ethylenically unsaturated moiety which can enter into a polymerization reaction. The polymerizable groups Q, at each end of the macromonomer, may be the same or different. Preferably Q is a group of the formula A

$$P_1\text{-}(Y)_m\text{-}(R'\text{-}X)_p\text{-} \qquad (A)$$

wherein $P_1$ is a free-radical-polymerizable group;

Y is —CONHCOO—, —CONHCONH—, —OCONHCO—, —NHCONHCO—, —NHCO—, —CONH—,

—NHCONH—, —COO—, —OCO—, —NHCOO— or —OCONH—;

m and p, independently of one another, are 0 or 1;

R' is a divalent radical of an organic compound having up to 20 carbon atoms;

$X_1$ is —NHCO—, —CONH—, —NHCONH—, —COO—, —OCO—, —NHCOO— or —OCONH—.

A free-radical-polymerizable group $P_1$ is, for example, alkenyl, alkenylaryl or alkenylarylenealkyl having up to 20 carbon atoms. Examples of alkenyl are vinyl, allyl, 1-propen-2-yl, 1-buten-2-, -3- and -4-yl, 2-buten-3-yl, and the isomers of pentenyl, hexenyl, octenyl, decenyl and undecenyl. Examples of alkenylaryl are vinylphenyl, vinylnaphthyl or allylphenyl. An example of alkenylarylenealkyl is o-, m-, or p-vinylbenzyl.

$P_1$ is preferably alkenyl or alkenylaryl having up to 12 carbon atoms, particularly preferably alkenyl having up to 8 carbon atoms, in particular alkenyl having up to 4 carbon atoms.

Y is preferably —COO—, —OCO—, —NHCONH—, —NHCOO—, —OCONH—, NHCO— or —CONH—, particularly preferably —COO—, —OCO—, NHCO— or —CONH—, and in particular, —COO— or —OCO—.

$X_1$ is preferably —NHCONH—, —NHCOO— or —OCONH—, particularly preferably —NHCOO— or —OCONH—.

In a preferred embodiment, the indices, m and p, are not simultaneously zero. If p is zero, m is preferably 1.

R' is preferably alkylene, arylene, a saturated bivalent cycloaliphatic group having 6 to 20 carbon atoms, arylenealkylene, alkylenearylene, alkylenearylenealkylene or arylenealkylenearylene.

Preferably, R' is a divalent radical having up to 12 carbon atoms, particularly preferably a divalent radical having up to 8 carbon atoms. In a preferred embodiment, R' is furthermore alkylene or arylene having up to 12 carbon atoms. A particularly preferred embodiment of R' is lower alkylene, in particular lower alkylene having up to 4 carbon atoms.

It is particularly preferred that Q be selected from the group consisting of acryloyl, methacryloyl, styryl, acrylamido, acrylamidoalkyl, urethanemethacrylate, or any substituted derivatives thereof. Most preferably Q is a compound of formula A wherein $P_1$ is alkenyl of up to 4 carbon atoms, Y is —COO—, R' is alkylene of up to 4 carbon atoms, $X_1$ is —NHCOO— and m and p are each one.

Suitable substituents may be selected from: alkyl, alkenyl, alkynyl, aryl, halo, haloalkyl, haloalkenyl, haloalkynyl, haloaryl, hydroxy, alkoxy, alkenyloxy, aryloxy, haloalkoxy, haloalkenyloxy, haloaryloxy, amino, alkylamino, alkenylamino, alkynyl-amino, arylamino, acyl, aroyl, alkenylacyl, arylacyl, acylamino, alkylsulphonyloxy, arylsulphenyloxy, heterocyclyl, heterocycyloxy, heterocycylamino, haloheterocyclyl, alkoxycarbonyl, alkylthio, alkylsulphonyl, arylthio, arylsulphonyl, aminosulphonyl, dialkylamino and dialkylsulphonyl, having up to 10 carbon atoms.

The linking group L may be any difunctional moiety able to react with hydroxyl. Suitable precursors to L are α,ω-diepoxides, α,ω-diisocyanates, α,ω-diisothiocyanates, α,ω-diacylhalides, α,ω-dithioacylhalides, α,ω-dicarboxylic acids, α,ω-dithiocarboxylic acids, α,ω-dianhydrides, α,ω-dilactones, α,ω-dialkylesters, α,ω-dihalides, α,ω-dialkylethers, α,ω-dihydroxymethylamides. It is preferred that the linking group be a bivalent residue (—C(O)—NH—R—NH—C(O)—) of a diisocyanate wherein R is a divalent organic radical having up to 20 carbon atoms.

The divalent radical R is, for example, alkylene, arylene, alkylenearylene, arylenealkylene or arylenealkylenearylene having up to 20 carbon atoms, a saturated bivalent cycloaliphatic group having 6 to 20 carbon atoms or cycloalkylenealkylenecycloalkylene having 7 to 20 carbon atoms.

In a preferred embodiment, R is alkylene, arylene, alkylenearylene, arylenealkylene or arylenealkylenearylene having up to 14 carbon atoms or a saturated divalent cycloaliphatic group having 6 to 14 carbon atoms. In a particularly preferred embodiment, R is alkylene or arylene having up to 12 carbon atoms or a saturated bivalent cycloaliphatic group having 6 to 14 carbon atoms.

In a preferred embodiment, R is alkylene or arylene having up to 10 carbon atoms or a saturated bivalent cycloaliphatic group having 6 to 10 carbon atoms.

In a particularly preferred meaning, R is a radical derived from a diisocyanate, for example from hexane 1,6-diisocyanate, 2,2,4-trimethylhexane 1,6-diisocyanate, tetramethylene diisocyanate, phenylene 1,4-diisocyanate, toluene 2,4-diisocyanate, toluene 2,6-diisocyanate, m- or p-tetramethylxylene diisocyanate, isophorone diisocyanate or cyclohexane 1,4-diisocyanate.

Aryl is a carbocyclic aromatic radical which is unsubstituted or substituted preferably by lower alkyl or lower alkoxy. Examples are phenyl, tolyl, xylyl, methoxyphenyl, t-butoxy-phenyl, naphthyl and phenanthryl.

Arylene is preferably phenylene or naphthylene, which is unsubstituted or substituted by lower alkyl or lower alkoxy, in particular 1,3-phenylene, 1,4-phenylene or methyl-1,4-phenylene, 1,5-naphthylene or 1,8-naphthylene.

A saturated bivalent cycloaliphatic group is preferably cycloalkylene, for example cyclohexylene or cyclohexylene (lower alkylene), for example cyclohexylenemethylene, which is unsubstituted or substituted by one or more lower alkyl groups, for example methyl groups, for example trimethylcyclohexylenemethylene, for example the bivalent isophorone radical.

For the purposes of the present invention, the term "lower" in connection with radicals and compounds, unless defined otherwise, denotes, in particular, radicals or compounds having up to 8 carbon atoms, preferably having up to 4 carbon atoms.

Lower alkyl has, in particular, up to 8 carbon atoms, preferably up to 4 carbon atoms, and is, for example, methyl, ethyl, propyl, butyl, tert-butyl, pentyl, hexyl or isohexyl.

Alkylene has up to 12 carbon atoms and can be straight-chain or branched. Suitable examples are decylene, octylene, hexylene, pentylene, butylene, propylene, ethylene, methylene, 2-propylene, 2-butylene, 3-pentylene, and the like.

Lower alkylene is alkylene having up to 8 carbon atoms, particularly preferably up to 4 carbon atoms. Particularly preferred meanings of lower alkylene are propylene, ethylene and methylene.

The arylene unit in alkylenearylene or arylenealkylene is preferably phenylene, unsubstituted or substituted by lower alkyl or lower alkoxy, and the alkylene unit therein is preferably lower alkylene, such as methylene or ethylene, in particular methylene. These radicals are therefore preferably phenylenemethylene or methylenephenylene.

Lower alkoxy has, in particular, up to 8 carbon atoms, preferably up to 4 carbon atoms, and is, for example, methoxy, ethoxy, propoxy, butoxy, tert-butoxy or hexyloxy.

Arylenealkylenearylene is preferably phenylene(lower alkylene)phenylene having up to 8, in particular up to 4, carbon atoms in the alkylene unit, for example phenyleneethylene-phenylene or phenylenemethylenephenylene.

Some examples of preferred diisocyanates from which bivalent residues are derived include trimethylhexamethyl-enediisocyanate (TMHMDI), isophorone diisocyanate (IPDI), methylenediphenyl diisocyanate (MDI) and 1,6-hexamethylene diisocyanate (HMDI).

Preferably, x in Formula II is in the range of from 0 to 20, more preferably in the range from 8 to 12, and y is in the range from 0 to 25, more preferably in the range from 10 to 14.

A preferred macromonomer is one in which n is in the range of from 1 to 4, L is the bivalent residue derived from trimethylhexamethylene diisocyanate (TMHMDI) and Q is the residue derived from isocyanatoethyl methacrylate.

A preferred embodiment of this invention is directed to a cell growth substrate polymer comprising a polymerized macromonomer of formula IV:

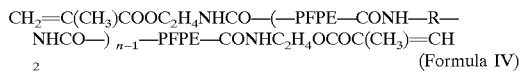

(Formula IV)

wherein PFPE is a perfluorinated polyether of formula II as herein defined, wherein x is in the range of from 8 to 10 and y is in the range of from 10 to 14, n>1.0, and R is alkylene or arylene having up to 12 carbon atoms or a saturated bivalent cycloaliphatic group having 6 to 14 carbon atoms.

In a particularly preferred embodiment of the present invention there is provided a cell growth substrate polymer comprising a polymerized macromonomer of formula III:

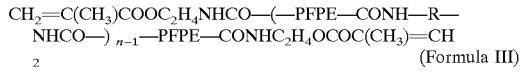

(Formula III)

wherein PFPE is a perfluorinated polyether of formula II as herein defined, n is at least 1.0, R is the trimethyl-hexamethylene component of TMHMDI, and wherein x is in the range of from 8 to 10 and y is in the range of from 10 to 14.

We have also found that unlike the attachment of endothelial cells and fibroblasts to synthetic polymers as described in the prior art, in the case of the telechelic perfluorinated polyether polymers the initial attachment of corneal epithelial cells is not dependent upon the adsorption of the glycoproteins fibronectin or vitronectin from the culture medium. Our findings show that the telechelic perfluorinated polyether polymers directly support adhesion of corneal epithelial cells.

In another aspect, this invention provides a material for the attachment and growth of human or animal cells in vitro, wherein the material comprises a cell growth substrate polymer as herein defined.

In another aspect, this invention provides a material for the attachment of human or animal cells in vivo, wherein the material comprises a cell growth substrate polymer as herein defined.

In another aspect, this invention provides a material for the attachment and growth of human or animal cells, the material comprising a cell growth substrate polymer as herein defined and additionally including adsorbed or coupled adhesive glycoproteins. Preferably, the adhesive glycoproteins are selected from the group consisting of fibronectin, vitronectin, collagen, laminin and thrombospondin.

In another aspect, this invention provides a process for the production of cell growth substrate polymers. The macromonomers of the present invention may be copolymerized or homopolymerized to afford transparent polymer in the presence of a suitable initiator. Standard methods well known in the art for effecting polymerization may be utilized, with free radical polymerization being preferred. Free radical polymerization can be simply carried out by irradiating (using ultraviolet light) monomer mixtures containing a UV initiator, such as benzoin methyl ether, in an appropriate container or vessel. The mixture is irradiated for a sufficient time to enable polymerization to take place. Alternately, thermal initiation using a thermal initiator, such as azobisisobutyronitrile, can be employed.

The macromonomer can be converted to polymer neat or in the presence of one or more solvents. While the structure of the macromonomer has the most significant effect on the resulting modulus, the choice of solvent and comonomer also has an effect. Useful solvents include those selected from the following classes: esters, alcohols, ethers, and halogenated solvents. Fluorinated solvents are particularly useful and their use in combination with other solvents (in ratios varying from 1:9 to 9:1) from the classes above is especially desirable. Solvent concentrations of between 0–70% w/w, particularly 10–50% w/w in the polymerization mixture are desirable. Preferred solvents include acetates, particularly isopropyl acetate and tert-butyl acetate, 2-(trifluoromethyl)-2-propanol, chlorofluoroalkanes, particularly trichlorotrifluoroethane, and perfluorinated alkanes, such as perfluoro-1,3-dimethylcyclohexane and the like.

Comonomers comprising one or more ethylenically unsaturated groups which can enter into a reaction to form a copolymer may be incorporated. It is preferred that the ethylenically unsaturated group be selected from the group consisting of acryloyl, methacryloyl, styryl, acrylamido, acrylamidoalkyl, urethanemethacrylate, or any substituted derivatives thereof. Suitable comonomers include fluorine- and silicon-containing alkyl acrylates and hydrophilic comonomers, which to one who is skilled in the art may be selected from a wide range of materials available, and mixtures thereof.

A comonomer present in the novel polymer can be hydrophilic or hydrophobic or a mixture thereof. Suitable comonomers are, in particular, those which are usually used in the production of contact lenses and biomedical materials. A hydrophobic comonomer is taken to mean a monomer which typically gives a homopolymer which is insoluble in water and can absorb less than 10% by weight of water. Analogously, a hydrophilic comonomer is taken to mean a monomer which typically gives a homopolymer which is soluble in water or can absorb at least 10% by weight of water.

Suitable hydrophobic comonomers are, without limitation thereto, $C_1$–$C_{18}$alkyl and $C_3$–$C_{18}$cycloalkyl acrylates and methacrylates, $C_3$–$C_{18}$alkylacrylamides and -methacrylamides, acrylonitrile, methacrylonitrile, vinyl $C_1$–$C_{18}$alkanoates, $C_2$–$C_{18}$alkenes, $C_2$–$C_{18}$haloalkenes, styrene, (lower alkyl)styrene, lower alkyl vinyl ethers, $C_2$–$C_{10}$perfluoroalkyl acrylates and methacrylates and correspondingly partially fluorinated acrylates and methacrylates, $C_3$–$C_{12}$perfluoroalkylethylthiocarbonylaminoethyl acrylates and methacrylates, acryloxy- and methacryloxyalkylsiloxanes, N-vinylcarbazole, $C_1$–$C_{12}$alkyl esters of maleic acid, fumaric acid, itaconic acid, mesaconic acid and the like.

Preference is given, for example, to acrylonitrile, $C_1$–$C_4$alkyl esters of vinylically unsaturated carboxylic acids having 3 to 5 carbon atoms or vinyl esters of carboxylic acids having up to 5 carbon atoms.

Examples of suitable hydrophobic comonomers are methyl acrylate, ethyl acrylate, propyl acrylate, isopropyl acrylate, cyclohexyl acrylate, 2-ethylhexyl acrylate, methyl methacrylate, ethyl methacrylate, propyl methacrylate, butyl acrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyltoluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl methacrylate, tristrimethylsilyloxysilylpropyl methacrylate (hereinafter: Tris methacrylate), tristrimethylsilyloxysilylpropyl acrylate (hereinafter: Tris acrylate), 3-methacryloxy propylpentamethyldisiloxane and bis(methacryloxypropyl) tetramethyldisiloxane.

Preferred examples of hydrophobic comonomers are methyl methacrylate, Tris acrylate, Tris methacrylate and acrylonitrile.

Suitable hydrophilic comonomers are, without this being an exhaustive list, hydroxyl-substituted lower alkyl acrylates and methacrylates, acrylamide, methacrylamide, (lower alkyl)-acrylamides and -methacrylamides, ethoxylated acrylates and methacrylates, hydroxyl-substituted (lower alkyl) acrylamides and -methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino(lower alkyl)- (where the term "amino" also includes quaternary ammonium), mono(lower alkylamino) (lower alkyl) and di(lower alkylamino) (lower alkyl) acrylates and methacrylates, allyl alcohol and the like. Preference is given, for example, to N-vinyl-2-pyrrolidone, acrylamide, methacrylamide, hydroxyl-substituted lower alkyl acrylates and methacrylates, hydroxy-substituted (lower alkyl) acrylamides and -methacrylamides and vinylically unsaturated carboxylic acids having a total of 3 to 5 carbon atoms.

Examples of suitable hydrophilic comonomers are hydroxyethyl methacrylate (HEMA), hydroxyethyl acrylate, hydroxypropyl acrylate, trimethylammonium 2-hydroxy propylmethacrylate hydrochloride (Blemer® QA, for example from Nippon Oil), dimethylaminoethyl methacrylate (DMAEMA), dimethylaminoethyl (meth)acrylamide, acrylamide, methacrylamide, N,N-dimethylacrylamide (DMA), allyl alcohol, vinylpyridine, glycerol methacrylate, N-(1,1-dimethyl-3-oxobutyl)acrylamide, N-vinyl-2-pyrrolidone (NVP), acrylic acid, methacrylic acid and the like.

Preferred hydrophilic comonomers are trimethylammonium 2-hydroxy propylmethacrylate hydrochloride, 2-hydroxyethyl methacrylate, dimethylaminoethyl methacrylate, trimethylammonium 2-hydroxypropylmethacrylate hydrochloride, N,N-dimethylacrylamide and N-vinyl-2-pyrrolidone.

Particularly preferred comonomers include dihydroperfluoroalkyl acrylates, such as dihydroperfluorooctyl acrylate and 1,1-dihydroperfluorobutyl acrylate, trihydroperfluoroalkyl acrylates, tetrahydroperfluoroalkyl acrylates, tris (trimethylsilyloxy)propyl methacrylate or acrylate, and amine-containing comonomers, such as N,N-dimethylaminoethyl methacrylate, N,N-dimethyl acrylamide and N,N-dimethylamino-ethylacrylamide. The preferred range for addition of individual comonomers into the formulation is from 0 to 60% by weight and most preferably 0 to 40% by weight of the formulation parts. Mixtures of macromonomers of formula I may also be used to make suitable copolymers with or without other comonomers.

A polymer network can, if desired, be reinforced by addition of a crosslinking agent, for example a polyunsaturated crosslinking comonomer. In this case, the term crosslinked polymers is used. The invention, th erefore, furthermore relates to a crosslinked polymer comprising the product of the polymerization of a macromer of the formula (I), if desired with at least one vinylic comonomer and with at least one crosslink ing comonomer.

Examples of typical crosslinking comonomers ar e allyl (meth)acrylate, lower alkylene glycol di(m eth)acrylate, poly(lower alkylene) glycol di(meth)acrylate, lower alkylene di(meth)acrylate, divinyl ether, divinyl sulfone, di- and trivinylbenzene, trimethylolpropane tri(meth)acrylate, pentaerythritol tetra(meth)acrylate, bisphenol A di(meth) acrylate, methylenebis(meth)acrylamide, triallyl phthalate and diallyl phthalate.

If a crosslinking comonomer is used, the amount used is in the range of from 0.05 to 20% of the expected total weight of polymer, preferably the comonomer is in the range of 0.1 to 10%, and more preferably in the range of 0.1% to 2%.

By way of example, in the manufacture of cell growth materials and implants of such polymers, the appropriate quantities of polymerizable monomers, solvent (if required) and photoinitiator are mixed together to form a polymerization mixture. The polymerization mixture is then flushed with nitrogen and the required quantity dispensed into an appropriate mould. The mould is closed and clamped and the assembly is placed into an irradiation cabinet equipped with 365 nm UV lamps. The irradiation is performed for the required time and then the halves of the mould are separated. The polymerized material is extracted in an appropriate solvent (for example, an isopropyl or tert-butylacetate/ fluorinated solvent mixture). The solvent is then exchanged with an alcohol (for example, isopropyl alcohol) and subsequently with saline to yield th e product.

The macromonomer may be polymerized to form the cell growth substrate polymer with other additives, such as adjuvants or growth factors including fibronectin, vitronectin, coliagen, laminin and thrombospondin.

As would be obvious to one skilled in the art, the polymerisation could also be carried out on the surface of another substrate or within a supporting matrix, so that the substrate would be coated with the perfluoropolyether polymer.

The cell growth substrate polymers of this invention may also be used to produce porous substrates. Porosity may be provided by the inherent porosity of the material. Alternatively, pores may be introduced into the polymers by various procedures such as those described in WO 90/07575, WO 91/07687, U.S. Pat. No. 5,244,799, U.S. Pat. No. 5,238,613, U.S. Pat. No. 4,799,931 and U.S. Pat. No. 5,213,721, the content of which are incorporated herein by reference.

With suitable selection, the resultant cell growth substrate polymer is optically transparent, having a refractive index that provides a good match with aqueous media, tissue and cellular material. As a result this polymer is ideal for use as an ocular prostheses, such as a cornea onlay or implant.

The polymers according to the invention may be formed into other useful cell growth substrates using conventional moulding and processing techniques as are well known in the art.

The polymers have properties that make them suitable as materials for the attachment and growth of human or animal cells in vivo or in vitro, medical implants (such as implantable semipermeable membrane materials, tissue implants in cosmetic surgery, implants containing hormone secreting cells such as pancreatic islet cells, breast implants, artificial joints, and the like), in artificial organs, tissue culture apparatus (such as bottles, trays, dishes and the like) in biological reactors (such as those used in the production of valuable proteins and other components by cell culture), in optical instruments, as microscope slides and the like.

Ocular prostheses, such as corneal implants, may be made by polymerization in moulds and, optionally, the resultant polymer may be fabricated or machined to the desired conformation. Ocular prostheses may be made by other methods which are well known per se to those skilled in the art. Porosity may be provided as described above.

Corneal implants may be placed by way of conventional surgical techniques beneath, within, or through corneal epithelial tissue, or within the corneal stroma or other tissue layers of the cornea. Such implants may change the optical properties of the cornea (such as to correct visual deficiencies) and/or change the appearance of the eye, such as pupil coloration. A corneal implant may comprise an optical axis region which on implantation covers the pupil and provides visual acuity, and a less transparent region which surrounds the periphery of the optical axis region. Alternatively the implant may have the same visual acuity across its dimensions.

It has been found that the flow of high molecular weight tissue fluid components such as proteins and glycoproteins (for example, growth factors, peptide and protein hormones, and proteins associated with the transport of essential metals) and the like across a corneal implant, that is, between epithelial cells and stromal cells and even the endothelial layer and beyond, is important for long term maintenance and viability of tissue anterior and posterior to a corneal implant. Accordingly the corneal implant is advantageously prepared with a porosity sufficient to allow passage therethrough of tissue fluid components having a molecular weight greater than about 10,000 daltons, thereby providing for a flux of tissue fluid components in addition to small molecular weight nutrients (such as glucose, fats and amino acids) and respiratory gases between cells anterior of the implant and cells posterior thereof.

Preferably a corneal implant has a porosity sufficient to admit proteins and other biological macromolecules of a molecular weight up to and greater than 10,000 daltons, such as from 10,000 to 1,000,000 daltons, but not sufficient to admit cells and thus tissue invasion into the optical axis region of the corneal onlay. Where porosity of the implant is provided by pores, the optical axis region comprises a plurality of pores, the number of which is not in any way limiting, but which is sufficient to provide flow of tissue components between the anterior and posterior regions of an implant. Preferably, the pores formed within the optical axis region do not cause refraction of visible light to an extent that would cause any problem with regard to vision correction. It is to be understood that the term pore does not put any geometric limitation on the nature of the pores which may be of regular or irregular morphology. It should be recognized that not all pores may be of the same diameter.

Outside of the optical axis region, the corneal implant may have the same porosity as the optical axis region. Alternatively, this region of the implant surrounding the periphery of the optical axis region, which may be referred to as the skirt, may allow the ingrowth of cells of the cornea thereby assisting in anchorage of the implant to the eye.

Porosity in the skirt may be an inherent feature of the material from which the skirt is formed. In this regard it is to be appreciated that the skirt may be formed of the same material as the optical axis region and may be integral therewith. In this situation, pores of differing diameter may be formed in the optical axis region and the skirt. Alternatively, the skirt may be formed of a different material from the optical axis region, which material is of a higher porosity than the optical axis region so as to allow this tissue ingrowth. Preferably the skirt may be comprised of an optically transparent polymer as is the optical axis region, but alternatively, the skirt may be comprised of an optically non-transparent material or may be made of a porous material that is not optically transparent.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

The present invention is further described in the following non-limiting examples. If not otherwise specified, all parts are by weight. Temperatures are in degrees Celsius. Molecular weights of macromers or polymers are number average molecular weights if not otherwise specified.

EXAMPLE 1

This example illustrates the preparation of the macromonomer of formula I (n=2.9), where Q is the residue derived from isocyanatoethyl methacrylate, L is the bivalent residue derived from trimethylhexamethylene diisocyanate (TMHMDI), x is 10 and y is 14. Into a 250 ml flask equipped with stirrer bar is placed 100 g of a commercially available hydroxy terminated PFPE (available from Minnesota Mining and Manufacturing Company, St Paul, Minn. as Experimental Product L-12875) of hydroxyl number 55.4. To this is added 6.76 g of distilled trimethylhexamethylenediisocyanate. The flask is shaken vigorously for several minutes, and then 0.06 g of dibutyltin dilaurate is added. After being shaken for several more minutes, the mixture is stirred overnight. A mild exotherm is observed during the first half hour. After sixteen hours, the infrared spectrum is run to confirm complete consumption of the isocyanate. To the reaction mixture is then added 5.36 g of freshly distilled isocyanatoethyl methacrylate. The flask is again vigorously shaken for several minutes and the mixture was stirred overnight. An infrared spectrum is recorded to confirm the disappearance of the isocyanate.

This procedure is a general one and with adjustments of stoichiometry other macromonomers of Formula I (n>1), where Q is the residue derived from isocyanatoethyl methacrylate and L is the bivalent residue derived from trimethylhexamethylene diisocyanate (TMHMDI), can be prepared.

EXAMPLE 2

The procedure set forth below is used to evaluate cell attachment and growth.

Disks 6 millimetres in diameter are cut from the polymers under evaluation and transferred to sterile vials each containing 5 millilitres of serum free DMEM/Ham'sF12 (ratio of 1:1, v/v) culture medium (SFM) and washed for a period of three weeks by changing the SFM once a week with a further 5 millilitres of fresh medium. Both the washed polymers and the polymer-conditioned SFM were stored under sterile conditions at 4° C. until required.

Cell Culture

Bovine corneal epithelial (BCEp) cells of limbal origin ranging between passages 2 to 6 are used for the various assays. The culture medium is composed of DMEM/Ham'sF12 (1:1), supplemented with 20% (v/v) foetal bovine serum (FBS), 5 $\mu$g/ml insulin, 5 $\mu$g/ml transferrin, 5 ng/ml selenious acid, 60 $\mu$g/ml penicillin and 100 $\mu$g/ml streptomycin. Cells are incubated at 37° C. in a humidified atmosphere of air containing 5% $CO_2$. Culture medium is changed every second day. For some of the growth assays, FBS depleted of the cell-adhesive serum glycoproteins vitronectin and fibronectin is used in parallel with intact FBS.

Bovine corneal fibroblast (BCF) cells were cultured by the method above with the exception that the culture medium was supplemented with 10% (v/v) foetal bovine serum. The BCF assays were performed by the methods below with BCF replacing BCEp cells.

Corneal Epithelial Cell Growth Assay

Growth assays are conducted as follows. Four replicates of each 6 millimetre diameter disk are placed into individual wells of a 96-well tissue-culture tray and rinsed with 100 $\mu$l of sterile SFM. BCEp cells are then seeded on to the samples at a density of $8.5 \times 10^3$ cells/well and cultured for six days. Equivalent cells are also seeded on to tissue culture polystyrene (TCPS) wells as a positive control reference surface. Time-point replicates are removed and fixed with formol saline at appropriate time intervals, then stored at 4° C. until required. Fixed cells are then stained with methylene blue to both visualize and quantify cell attachment. Cell attachment is determined calorimetrically on a plate-reader and absorbances are expressed as a mean (±sd) percentage of that found for cells on tissue culture polystyrene (TCPS).

Corneal Epithelial Outgrowth Assay—Explant Outgrowth Assay

Six millimetres diameter buttons of bovine corneal tissue, from which the endothelium and >90% of the stroma has been removed, are set up on duplicate samples. The explants are cultured in the absence of serum in a culture medium consisting of DMEM/Ham's F12 supplemented with ITS (5 $\mu$g/ml insulin, 5 $\mu$g/ml transferrin, 5 $\mu$g/ml selenious acid), 1% (v/v) non-essential amino acids, 60 $\mu$g/ml penicillin and 100 $\mu$g/ml streptomycin. Outgrowth is monitored for a period of eight days, with changes of medium at day three and day six, after which the outgrowth areas are measured by image analysis (Quantimet 570, Leica Cambridge). An index of migration is calculated by dividing the final spreading area of each explant by its initial tissue area. Explants cultured on tissue culture polystyrene (TCPS) which is treated by corona discharge to optimize cellular attachment and growth are used as comparative control.

EXAMPLE 3

The following composition is placed in a polypropylene flat mould (0.5 mm thick) and polymerized for 16 h under irradiation from 365 nm UV lamps.

|  | Parts by weight |
|---|---|
| Macromonomer of Example 1 (n = 2.9) | 80 |
| Isopropyl acetate | 20 |
| Benzoin methyl ether | 0.3 |

After demoulding, the resulting flat discs were extracted at 37° C. in PF5060 (a commercially available perfluorinated solvent obtained from Minnesota Mining and Manufacturing Company (3M)) for three hours, then placed in isopropyl acetate (IPAc) overnight, then in a 50/50 (v/v) mix of IPAc—isopropyl alcohol (IPA) for three hours and into fresh IPA for a further three hours. The discs were then dried overnight at 30° C. in a vacuum oven on filter paper before being hydrated in saline for several days. The sessile contact angle of the polymer was 94 degrees. The hydrated polymeric discs were then examined for corneal cell attachment and growth as described in Example 2, and compared with tissue culture polystyrene as a positive control.

After seven days culture the relative level of attachment and growth of BCEp cells to the polymer disks was 80±10.7% of that on the positive control surface (tissue culture polystyrene (TCPS)) while the attachment of BCF was 72.3±8.8% of that on TCPS.

This shows that the polymer possesses similar activity to tissue culture polystyrene for promoting cell attachment and growth. The morphology of the cells on the polymer surface was of well spread cells, similar in morphology to the cells on the tissue culture polystyrene (TCPS) surface.

EXAMPLE 4

The following composition is placed in a polypropylene flat mould (0.5 mm thick) and polymerized for 16 h under irradiation from 365 nm UV lamps:

|  | Parts by weight |
|---|---|
| Macromonomer of Example 1 (n = 2.9) | 60 |
| Dihydroperfluorooctyl acrylate (DHPFOA) | 5 |
| N,N-dimethylaminoethyl methacrylate (DMAEMA) | 20 |
| Isopropyl acetate | 20 |
| Benzoin methyl ether | 0.3 |

After demoulding, the resulting flat discs were extracted at room temperature in PF5060 (a commercially available perfluorinated solvent obtained from Minnesota Mining and Manufacturing Company (3M)) for three hours, then placed in isopropyl acetate (IPAc) overnight, then in a 50/50 (v/v) mix of IPAc—isopropyl alcohol (IPA) for three hours and into fresh IPA for a further three hours. The discs were then dried overnight at 30° C. in a vacuum oven on filter paper before being hydrated in saline for several days and then examined for corneal cell attachment and growth as described in Example 2, using tissue culture polystyrene as a positive control. This polymer displayed good cell attachment, equivalent to that of tissue culture polystyrene at day one. At day six, there is good cell growth with the number of cells present being approximately 80% of that of tissue culture polystyrene.

Polymers were also produced according to the above procedure where the DHPFOA content was 10, 15 and 20 parts by weight, while maintaining the relative proportions of macromonomer of Example 1 (at 60 parts by weight), DMAEMA (20 parts) and IPAc (20 parts).

EXAMPLE 5

Formulations of the following compositions, with the N,N-dimethylaminoethyl methacrylate (DMAEMA) content ranging from 0% to 20% (w/w), were placed in polypropylene flat moulds (0.5 mm thick) and polymerized for 16h under irradiation from 365 nm UV lamps:

| Polymer | Parts Macro-monomer of Example 1 (n = 2.9) by weight | Parts N,N-dimethyl aminoethyl methacrylate (DMAEMA) by weight | Parts Iso propyl acetate by weight | Parts Benzoin methyl ether by weight |
| --- | --- | --- | --- | --- |
| 5.1 | 80 | 0 | 20 | 0.3 |
| 5.2 | 75 | 5 | 20 | 0.3 |
| 5.3 | 70 | 10 | 20 | 0.3 |
| 5.4 | 65 | 15 | 20 | 0.3 |
| 5.5 | 60 | 20 | 20 | 0.3 |

After demoulding, the resulting flat discs were extracted using the procedure of Example 4 and then evaluated for bovine corneal epithelial attachment as described in Example 2 above, using bovine corneal epithelial cells of peripheral origin at passage 4 for the attachment assay.

Initial cell attachment was investigated after a ninety minute incubation period, followed by a longer, twenty four hour attachment on the same series of polymers. After ninety minutes incubation all the test samples supported cell attachment. Cell numbers on the 5% and 10% N,N-dimethylaminoethyl methacrylate (DMAEMA) content polymers were similar to those found on the tissue culture polystyrene (TCPS) control surface, whilst the 0% and 20% N,N-dimethylaminoethyl methacrylate (DMAEMA) content polymers have slightly reduced but very significantly positive levels of adhesion. The cells on the test samples are generally well spread, albeit slightly less well spread compared to those on the tissue culture polystyrene (TCPS) surface, with the 20% N,N-dimethylaminoethyl methacrylate (DMAEMA) content group showing the closest morphology to the tissue culture polystyrene (TCPS) set. Distribution of the cells is uniform across the whole of the test polymer surfaces. After twenty four hours incubation cells remain attached to all of the test surfaces and the relative number of cells on all test polymers is found to be very similar to those on the tissue culture polystyrene (TCPS) reference surface. The morphology found on the 10% N,N-dimethylaminoethyl methacrylate (DMAEMA) content samples is similar to the cells on tissue culture polystyrene (TCPS) whilst those on the 5% N,N-dimethylaminoethyl methacrylate (DMAEMA) content set show a more uniform distribution than either 0% or tissue culture polystyrene (TCPS). Cells on the 20% N,N-dimethylaminoethyl methacrylate (DMAEMA) content samples appear better spread than the 10%, with generally a more uniform distribution across the surface, but the 10% are generally supportive of cell attachment.

Overall, the rates of cell attachment appear similar to those found on tissue culture polystyrene (TCPS). For the 10% and 5% N,N-dimethylaminoethyl methacrylate (DMAEMA) content polymers, the cell morphology is comparable to that of bovine corneal epithelial cells attached to the tissue culture polystyrene (TCPS) surface.

In a separate study the polymer discs after demoulding were extracted as described in Example 3 and then examined for bovine corneal epithelial and fibroblast attachment as described in Example 2 above. The results after seven days are shown in Table A and indicate that this polymer supports the attachment and growth of bovine corneal epithelial cells and bovine corneal stromal fibroblasts. The morphology of the cells on the polymer surface is of well spread cells, similar in morphology to the cells on the tissue culture polystyrene surface.

TABLE A

| Polymer | Number of BCEp cells attached relative to TCPS (±sd) | Number of BCF cells attached relative to TCPS (±sd) |
| --- | --- | --- |
| TCPS | 100.0 (±0.0)% | 100.0 (±0.0)% |
| 5.1 | 80.1 (±10.7)% | 72.3 (±8.8)% |
| 5.2 | 59.5 (±17.2)% | 40.4 (±2.5)% |

EXAMPLE 6

The polymers prepared according to Examples 3 and 4 are tested for cellular attachment and growth according to the procedure of Example 2, using intact FBS, or FBS depleted of the cell adhesive serum glycoproteins, vitronectin and fibronectin. As a positive control reference, surface cell growth and attachment is assayed on tissue culture polystyrene.

Over a six day culture period, the polymers of Examples 3 and 4 surprisingly supported the attachment and growth of BCEp cells to a very significant extent. These results were quite unexpected from the results obtained previously with other cells, for example, endothelial cells and us ing hydrophobic or hydrophilic polymer surfaces where cellular attachment does not take place to any appreciable extent. This attachment and growth of the corneal epithelial cells was not dependent upon the adsorption onto the surface of the polymers of either exogenous fibronectin or exogenous fibronectin or exogenous vitronectin. These results indicate that the surface chemistry of the polymers is suitable for the attachment and growth of corneal epithelial cells by a mechanism that involves direct binding of the cells to the polymer surface. The surface of the polymeric materials can also support attachment of corneal epithelial cells by a mechanism that involves the adsorption or presence on the polymer surface of glycoproteins that contain binding sites for cells, such as fibronectin and vitronectin.

EXAMPLE 7

In the Examples above, it is shown that the polymers of the invention support the attachment and growth of corneal cells and are suitable biomaterials for use in ocular implants. However, it is also found that the performance of the polymers in longer-term cell growth assays can be suboptimal unless the polymers are adequately treated to remove extractables. If extractables are not effectively removed from the polymers, then the attachment and growth of corneal epithelial cells on the polymers is inhibited. This example demonstrates suitable extraction methods.

A polymer formulation consisting of the macromonomer of Example 1 (n=2.9), (60% w/w), dihydroperfluorooctyl acrylate (20% w/w), initiator (benzoin methyl ether, 0.3% w/w) and solvent (isopropyl acetate, 20% w/w) is cast into 0.2 mm flat molds and polymerised under U.V. irradiation (350 nm) for 3 hours. After curing is complete, the "flats" are removed from the molds and dried overnight on filter paper in a vacuum oven at 35° C. At this stage, the polymeric flats are extracted by one of the following different extraction procedures using a volume of solvent for each extraction step of 50 ml for 5 flats.

Extraction Method 1

The flats are extracted and hydrated using the method of Example 4 above. Approximately 5.03% of the original weight is extracted. These polymers are designated "Method 1" in Table 1.

Extraction Method 2

The flats are extracted at room temperature in PF5060 for 6 hours, then placed in isopropyl acetate (IPAc) overnight, then in a 50/50 (v/v) mix of IPAc/iso- propyl alcohol (IPA) for 3 hours and into fresh IPA for a further 3 hours. The flats are then dried overnight in a vacuum oven on filter paper, before being hydrated in saline for several days. Approximately 5.20% of the original weight is extracted. These polymers are designated "Method 2" in Table 1.

Extraction Method 3

The flats are extracted at 37° C. in PF5060 for 3 hours, then placed in isopropyl acetate (IPAc) overnight, then in a 50/50 (v/v) mix of IPAc/isopropyl alcohol (IPA) for 3 hours and into fresh IPA for a further 3 hours. The flats are then dried overnight in a vacuum oven on filter paper, before being hydrated in saline for several days. Approximately 5.45% of the original weight is extracted. These polymers are designated "Method 3" in Table 1.

Extraction Method 4

The flats are extracted at room temperature in PF5060 for 3 hours, then placed in diisopropyl ether overnight, followed by extraction with IPAc overnight, then in a 50/50 (v/v) mix of IPAc/isopropyl alcohol (IPA) for 3 hours and into fresh IPA for a further 3 hours. All of these extraction steps are conducted at room temperature. The flats are then dried overnight in a vacuum oven on filter paper, before being hydrated in saline for several days. Approximately 5.00% of the original weight is extracted. These polymers are designated "Method 4" in Table 1.

Cell Culture and Growth Assay

The polymer flats extracted by one of these methods are transferred to McCartney bottles containing phosphate buffered saline, pH 7.4 (PBS), and autoclaved for 20 minutes at 121° C. and 105 kPa. Disks of 6 mm diameter are then cut from the autoclaved materials with a sterile dermapunch and replicates placed into individual wells of a 96-well tissue-culture tray. Bovine corneal epithelial cells are then seeded into each well at $5 \times 10^4$ cells/ml and cultured for a period of four days. The number of adherent cells on the extracted samples are determined calorimetrically and expressed as a mean percentage (±standard deviation) of the mean number of cells attached to a control tissue culture polystyrene (TCPS) surface in Table 1.

TABLE 1

Effect of Extraction Method

| Extraction Method | Number of Cells Attached Relative to TCPS % (±std dev) |
| --- | --- |
| Method 1 | 118.7 (±4.8) |
| Method 2 | 121.9 (±1.2) |
| Method 3 | 134.3 (±9.7) |
| Method 4 | 103.3 (±6.2) |
| TCPS Standard | 100 (±6.1) |

Table 1 shows that the polymers extracted by one of these four extraction methods (Methods 1–4) support the attachment and growth of corneal epithelial cells during a four day culture period to a level that is equivalent to, or slightly better than, that of the tissue culture polystyrene (TCPS) surface that is the positive control. Each of these four extraction methods successfully remove leachable cytotoxic component(s) from the copolymer. The level of growth of bovine corneal epithelial cells on the polymer after extraction by these methods is at a level found on polymer samples that had been extracted over a three week period with serum-free culture medium.

EXAMPLE 8 ("Z 1.0")

A macromonomer of formula 1 (n=1) was obtained from Minnesota Mining and Manufacturing Company, St Paul, Minn., USA as experimental product L-9629. The following composition is placed in a polypropylene flat mould (0.5 mm thick) and polymerized for 16 h under irradiation from 365 nm UV lamps:

|  | Parts by weight |
| --- | --- |
| Macromonomer of Formula 1 (n = 1) | 80 |
| Isopropyl acetate | 20 |
| Benzoin methyl ether | 0.3 |

After demoulding, the polymer disks are extracted as described in Example 3 above, to give a clear polymer with a sessile contact angle of 125°, and then examined for bovine corneal epithelial and fibroblast attachment as described in Example 2 relative to tissue culture polystyrene. The results are shown in Table 2 and indicate that this polymer supports the attachment and growth of corneal epithelial cells and corneal stromal fibroblasts. The morphology of the cells on the polymer surface is of well spread cells, similar in morphology to the cells on the tissue culture polystyrene surface. Table 3 shows the relative ability of the polymer to support the outgrowth of corneal tissue from a button of corneal tissue as compared with the positive control tissue culture polystyrene. The explant growth assay was conducted for a culture period of 8 days. The table shows that this polymer supports the migration out into the polymer of corneal epithelial tissue.

TABLE 2

Cell Attachment Studies

| Example | Polymer Name | Number of Cells Attached Relative to TCPS % (±std dev) | |
| --- | --- | --- | --- |
| | | BCEp | BCF |
| | TCPS | 100.0 (±2.0) | 100.0 (±0.3) |
| Example 8 | Z 1.0 | 96.5 (±1.0) | 63.6 (±4.0) |
| Example 9 | Z 2.0 | 66.3 (±2.0) | 69.4 (±0.6) |
| Example 3 | Z 2.9 | 95.0 (±4.0) | 92.6 (±2.3) |
| Example 10 | Z 4.0 | 71.8 (±6.1) | 4.6 (±1.5) |
| Example 11 | Z 1.2 | 77.1 (±6.9) | |
| Example 12 | Z 1.3 | 64.9 (±6.1) | |

TABLE 3

Outgrowth Studies

| Example | Polymer Name | Migration index (±std dev) |
| --- | --- | --- |
| | TCPS | 4.6 (±0.1) |
| Example 8 | Z 1.0 | 2.8 (±0.6) |
| Example 9 | Z 2.0 | 3.2 (±0.6) |
| Example 3 | Z 2.9 | 4.1 (±0.6) |
| Example 10 | Z 4.0 | 2.7 (±0.3) |
| Example 11 | Z 1.2 | 5.7 (±0.3) |
| Example 12 | Z 1.3 | 6.3 (±0.3) |

EXAMPLE 9 ("Z 2.0")

A macromonomer of formula 1 (n=2) was prepared using the general procedure described in Example 1. The following composition is placed in a polypropylene flat mould (0.5 mm thick) and polymerized for 16 h under irradiation from 365 nm UV lamps:

| | Parts by weight |
| --- | --- |
| Macromonomer of Formula 1 (n = 2) | 80 |
| Isopropyl acetate | 20 |
| Benzoin methyl ether | 0.3 |

After demoulding, the polymer disks are extracted as described in Example 3, to give a clear polymer with a sessile contact angle of 109°, and then examined for bovine corneal epithelial and fibroblast attachment as described in Example 2 above. The results are shown in Table 2 and indicate that this polymer supports the attachment and growth of corneal epithelial cells and corneal stromal fibroblasts. The morphology of the cells on the polymer surface is of well spread cells, similar in morphology to the cells on the tissue culture polystyrene surface. Table 3 shows the relative ability of the polymer to support the outgrowth of corneal tissue from a button of corneal tissue as compared with the positive control tissue culture polystyrene. The explant growth assay was conducted for a culture period of 8 days. The table shows that this polymer supports the migration out into the polymer of corneal epithelial tissue.

EXAMPLE 10 ("Z 4.0")

A macromonomer of formula 1 (n=4) was prepared using the general procedure described in Example 1. The following composition is placed in a polypropylene flat mould (0.5 mm thick) and polymerized for 16 h under irradiation from 365 nm UV lamps:

| | Parts by weight |
| --- | --- |
| Macromonomer of Formula 1 (n = 4) | 80 |
| Isopropyl acetate | 20 |
| Benzoin methyl ether | 0.3 |

After demoulding, the hydrophobic polymer disks are extracted as described in Example 3 above, to give a clear polymer with a sessile contact angle of 116, and then examined for bovine corneal epithelial and fibroblast attachment as described in Example 2 above. The results are shown in Table 2 and indicate that this polymer supports the attachment and growth of corneal epithelial cells and corneal stromal fibroblasts. The morphology of the cells on the polymer surface is of well spread cells, similar in morphology to the cells on the tissue culture polystyrene surface. Table 3 shows the relative ability of the polymer to support the outgrowth of corneal tissue from a button of corneal tissue as compared with the positive control tissue culture polystyrene. The explant growth assay was conducted for a culture period of 8 days. The table shows that this polymer supports the migration out into the polymer of corneal epithelial tissue.

EXAMPLE 11 ("Z 1.2")

Preparation of microporous polymer discs: The porous polymer discs were synthesised by the ultraviolet (UV) radical initiated polymerization of the thermodynamically stable, transparent, homogenous mixtures containing a macromonomer of formula I (n=1) and isopropanol. Macromonomer of formula I (n=1) was obtained from Minnesota Mining and Manufacturing Company, St. Paul, Minn., USA as experimental product L-9629. (L-9629 is a perfluoropolyether which is end capped with two polymerizable methacrylate functionalities and has an approximate molecular weight of 2000). The following composition is used in the manufacture of these discs:

| | Parts by weight |
| --- | --- |
| Macromonomer of Formula I (n = 1) | 54 |
| Isopropanol | 43 |
| Zonyl FS-300 (Du Pont) | 2.25 |
| Darocur 1173 (Ciba-Geigy) | 0.15 |

The macromonomer, solvent and surfactant were added to a glass screw capped vial furnished with a PTFE coated magnetic stirrer bar. The glass vial was then placed on a magnetic stirrer plate for ten minutes to allow thorough mixing of the three components. The free radical initiator Darocur 1173 then was added and mixing continued for a further five minutes. The resulting mixture was then placed under nitrogen into polypropylene flat moulds (0.2 mm thick) and polymerized for 3 h under irradiation from 365 nm UV lamps After polymerization was complete, the resulting flat polymeric discs were demoulded and extracted in isopropanol overnight (using 60 ml of solvent for every 10 discs). The solvent was then decanted off and replaced by isopropyl acetate. After standing at 37° C. for 4 hours, this solvent was then replaced by PF5060. After a further four hours at 37° C. the PF5060 was decanted and the discs were allowed to stand at room temperature until the excess PF5060 evaporated. The discs were finally stored in ethanol.

By this procedure, the polymer of Example 8 was obtained in microporous form as flat disks. The "hydrated" water content (% w/w) of the resulting porous discs was determined by comparing the hydrated and dehydrated weight of the discs. The discs were dried overnight in a vacuum oven at 37° C. then weighed. Hydration was achieved via a graded solvent exchange process from ethanol, 75% ethanol-water, 50% ethanol-water, 25% ethanol-water then finally water. The discs spend approximately five minutes in each solution. The hydrated discs are then placed on fine grade lint free tissue to pat dry the excess surface moisture and finally weighed as the hydrated weight. The water content of the hydrated discs determined by this procedure was 52%. The permeabilities of the discs to glucose (Molecular Weight=181), inulin (Molecular Weight=5,500) and albumin (Molecular Weight=67,000) were determined to be:

|  | Permeability cm/s |
| --- | --- |
| Glucose | $2.1 \times 10^{-4}$ |
| Inulin | $8.3 \times 10^{-5}$ |
| Albumin | $1.4 \times 10^{-5}$ |

The permeability of the perfluorinated discs were measured with reference to the permeabilities of glucose, inulin and albumin through Nuclepore 50 nm and Poretics 25 nm pore diameter discs, the porosities of which PCT/EP94/03680 teaches is suitable for an artificial corneal onlay.

|  | Permeability cm/s | | |
| --- | --- | --- | --- |
|  | Glucose | Inulin | Albumin |
| Nuclepore 50 nm | $4.7 \times 10^{-4}$ | $1.7 \times 10^{-4}$ | $2.2 \times 10^{-5}$ |
| Poretics 25 nm | $4.6 \times 10^{-5}$ | $1.1 \times 10^{-5}$ | $0.6 \times 10^{-6}$ |

This shows that the polymer of this example has a porosity intermediate between the Nuleopore and Poretics membrane and thus is of suitable porosity to provide an adequate flux of nutrients and high molecular weight proteins for a corneal onlay.

The porous polymer was examined for bovine corneal epithelial and fibroblast attachment as described in Example 2. The results are shown in Table 2 and indicate that this polymer supports the attachment and growth of corneal epithelial cells and corneal stromal fibroblasts. The morphology of the cells on the polymer surface is of well spread cells, similar in morphology to the cells on the tissue culture polystyrene surface. Table 3 shows the relative ability of the polymer to support the outgrowth of corneal tissue from a button of corneal tissue as compared with the positive control tissue culture polystyrene. The explant growth assay was conducted for a culture period of 8 days. The table shows that this polymer supports the migration of corneal epithelial tissue out into the polymer and is superior to tissue culture polystyrene for this purpose.

EXAMPLE 12 ("Z 1.3")

The polymer of Example 8 was obtained in an alternative microporous disk form. The following mixture was cast in 7×10 polypropylene membrane molds and polymerized for three hours over broad spectrum UV lamps using an identical protocol to that in Example 11.

|  | Parts by weight |
| --- | --- |
| Macromonomer of Formula I (n = 1) | 70 |
| Isopropanol | 35 |
| Darocur 1173 (Ciba-Geigy) | 0.19 |

Using the method outlined in example 11, the water content was determined to be 33%. The permeability was as follows:

|  | Permeability cm/s |
| --- | --- |
| Glucose | $9.18 \times 10^{-5}$ |
| Inulin | $3.21 \times 10^{-5}$ |
| Albumin | $0.86 \times 10^{-5}$ |

The porous polymer was examined for bovine corneal epithelial and fibroblast attachment as described in Example 2. The results are shown in Table 2 and indicate that this polymer supports the attachment and growth of cornea epithelial cells and corneal stromal fibroblasts. The morphology of the cells on the polymer surface is of well spread cells, similar in morphology to the cells on the tissue culture polystyrene surface. Table 3 shows the relative ability of the polymer to support the outgrowth of corneal tissue from a button of corneal tissue as compared with the positive control tissue culture polystyrene. The explant growth assay was conducted for a culture period of 8 days. The table shows that this polymer supports the migration of corneal epithelial tissue out into the polymer and is superior to tissue culture polystyrene for this purpose.

EXAMPLE 13 ("Z 1.1")

The polymer of Example 8 was obtained in an alternative microporous disc form. The following mixture was cast in 7×10 polypropylene membrane molds and polymerized for three hours over broad spectrum UV lamps using an identical protocol to that in Example 11.

|  | Parts by weight |
| --- | --- |
| Macromonomer of Formula I (n = 1) | 40 |
| Isopropanol | 40 |
| Zonyl FS-300 (Du Pont) | 12 |
| Darocur 1173 (Ciba-Geigy) | 0.31 |

Using the method outlined in example 11 the water content was determined to be 52%. The permeability was:

|  | Permeability cm/s |
| --- | --- |
| Glucose | $1.2 \times 10^{-4}$ |
| Inulin | $4.5 \times 10^{-5}$ |
| Albumin | $0.8 \times 10^{-5}$ |

This porous polymer is evaluated for its ability to support corneal tissue outgrowth on eye. The specific aim is to assess the performance of lenticules with regard to support of the intitial attachment, overgrowth and persistance of adhesion of corneal epithelial cells in vivo The lenticules are obtained by cutting the polymer of example 8 (0.2 mm thick) with a trephine of 4 mm diameter.

Methods of Implantation and Clinical Observation

The methods and performance of the study described in the following text was approved by the Animal Ethics Committee of The University of New South Wales. Five adult cats ranging in age from 2–4 years were used in the study. All the cats were free of active ocular or systemic diseases. Baseline measurements of corneal integrity, including slit-lamp evaluation and measurement of corneal thickness with an ultrasonic pachometer (VIDA 55), were conducted. Prior to implantation, all animals had the nictitating membranes removed from both eyes. One eye of each cat was chosen at random for implantation. Surgery was performed at a minimum of two weeks following removal of the nictitating membranes, by the following protocol. The cat was anaesthetised using 15 to 20 mg/kg body weight of ketamine and 0.5 to 1 mg/kg body weight of Xylazine intramuscularly to a depth of stage 3—plane 2. The central cornea was marked with a 4 mm diameter trephine (set to 20 $\mu$m depth). The epithelium within the marked area was removed by scraping with a beaver blader. A 2 mm diameter trephine (set to 100–150 $\mu$m) was used to perform a circular keratotomy in the central cornea. A 2 mm wide annular stromal pocket, extending towards the limbus, was prepared at the base of the keratotomy with a sharp-edged corneal dissector. The superior section of the pocket was extended towards the superior limbus by a further 3 mm so that the superior edge of the pocket was approximately 5 mm from the pocket mouth. An arcuate incision of 5 mm length at pocket depth was made along the superior edge of pocket with a beaver blade. The lenticule was placed into the stromal pocket through this incision using a flat spatula. The incision was then closed with 4–5 interrupted sutures of 10-0 nylon thread. Sofradex (0.5,% Framycetin Sulphate and 0.5,% Dexamethasone Sodium) eye drops were administered topically to the operated eye following surgery. Postoperative care included topical administration of steroids and antibiotics for the operated eye (Sofradex eye drops applied three times daily, plus 0.5% Chloromycetin ointment applied nightly) for 2 weeks. This regimen was reduced to once daily for the remainder of the observation period. The sutures were removed 5 weeks after surgery.

The clinical observation of the implanted eyes was as follows. The operated eyes were examined with a slit lamp, with both general appearance and fluorescein staining examined. Epithelial growth over the surface of the lenticule was quantitated using a grading system (described below). The severity of postoperative complications (if any) and the integrity of the implant were also assessed. All animals were assessed for approximately 9 weeks. After 63–68 days, the animals were terminated and both the implanted and control eyes assessed histologically (see below for histological techniques). Note: Had any severe complications such as corneal ulceration, inflammation or anterior stromal melting with lenticule protrusion been observed, the animal would have been terminated immediately using a lethal overdose of sodium pentobarbitone; however no animal included in this trial developed any such complications.

Clinical Scoring System Used for Grading Tissue Response to the Implanted Lenticules:

Parameter: No epithelium covering the lenticule surface: Score=0

Parameter: Epithelium covers 25% of the lenticule surface: Score=1

Parameter: Epithelium covers 50% of the lenticule surface: Score=2

Parameter: Epithelium covers 75% of the lenticule surface: Score=3

Parameter: Epithelium covers 100% of the lenticule surface: Score=4

Parameter: Full thickness epithelium covers 100% of the lenticule surface: Score=5.

This scoring method was used for the clinical evaluation.

Implants surgically placed into 5 cats were observed clinically for a period of 63—68 days. In all cases, overgrowth of corneal epithelial tissue was observed to commence within the first 3 days after surgery, and full coverage of the implant with epithelium was observed following 5–18 days (mean value of 10 days). Although there was some loss of epithelial coverage seen following this initial coverage, the epithelial tissue regrew and coverage was regained. Table 5 describes the clinical features of the epithelial coverage.

TABLE 5

| | | Clinical features of epithelial growth and complications | | | | |
|---|---|---|---|---|---|---|
| Cat | Observation period (Days) | Days to initial growth of epithelium | Days to full coverage of epithelium | Days to epithelial loss/regrowth (Location) | Clinical scores on termination | Complications (Day of onset) |
| A | 64 | 1 | 18 | 16/18 (most areas) 29/32 (central) 33/36 (central) 49/54 (nasal) 55/— (central) | 3 | anterior stromal melting (12) |
| B | 63 | 1 | 5 | 26/28 (central) 32/36 (superior) 63/— (central) | 3.7 | anterior stromal melting (54) |
| C | 63 | 1 | 6 | 12/14 (central) 48/49 (central) | 5 | anterior stromal melting (24) vascularization (52) |
| D | 65 | 2 | 12 | 55/59 (inferior) | 1 | anterior stromal melting (4) |
| E | 68 | 3 | 11 | 42/47 (central) | 4.5 | anterior stromal melting (9) |

Methods for Immunohistological Evaluation of Implants

Immunohistochemical evaluation of frozen sections of corneal tissue was performed by the following procedure. Freshly excised corneas are held in cold PBS and trimmed to provide limbus-to-limbus strips across the cornea. Tissue for frozen sections are used unfixed to preserve the antigenic sites. The strips of cornea are embedded in Tissue Tek OCT (Miles, USA) and snap frozen onto a metal chuck with carbon dioxide gas (CIG, Australia). Frozen transverse sections are cut at 7–8 $\mu$m using a cryostat (SLEE, UK) at −20° C. Sections are collected onto chrome-alum gelatin coated glass microscope slides, dried at 37° C. and then are individually wrapped in foil and stored at −70° C. Prior to use, sections are brought to room temperature for 15 minutes, unwrapped and dried at 37° C. for 5 minutes. Sections are incubated for 60 minutes at room temperature in a solution of 2% (w/v) bovine serum albumin (BSA, Fraction V from Boehringer-Mannheim, Germany) in PBS to reduce non-specific binding.

After blocking, sections are covered with the selected primary antibody (refer to Table 4) at a dilution of 1/100 in 1% (w/v) BSA and are rocked gently for 30 minutes at room temperature, with a further incubation of 30 minutes at 37° C. After three rinses in PBS, sections are covered with an appropriate fluoroscein isothiocyanate-conjugated secondary antibody (refer to Table 4) and rocked gently for 30 minutes at room temperature, followed by a 30 minute incubation at 37° C. Sections are protected from light during this incubation. Following three rinses in PBS, and a final rinse in double distilled water, sections are mounted in glycerol/PBS and are viewed on the same day as staining. Negative controls are routinely conducted with every experimental run involving an antibody stain. These are provided by incubating similar sections of corneal tissue in a 1/100 dilution of pre-immune serum (to match the species in which the primary antibody is raised) in place of the primary antibody, followed by the fluorescent secondary antibody being used for the test sections. All sections are viewed using a Nikon diaphot microscope equipped with an argon laser source (MRC-500 from BioRad Laboratories, USA). This yields dual phase/fluorescent images, which are photographed using colour transparency film.

TABLE 4

Primary and secondary antibodies used in immunocytochemistry

| To identify | Primary antibody used | Secondary antibody used |
|---|---|---|
| Epithelial tissue | AE5 against cytokeratin 3 (ICN #69-143) | Rabbit anti-mouse IgG FITC* (Dakopatts #F-232) |
| Adhesion complex components | Bullous pemphigoid antisera (Gift from hospital) | Rabbit anti-human IgG FITC* (Dakopatts #F-202) |

*FITC = fluoroscein isothiocyanate conjugated

The corneal epithelial tissue coverage of one of the implants was evaluated by immunohistochemical staining for epithelial cytokeratins and for the presence of components of Adhesion Complexes. The tissue coverage on the anterior surface of the implant was confirmed to be epithelial, through positive immunostaining with the AE5 antiserum. Furthermore, the basal cells of the epithelial coverage of the implant was shown to have positive immunostaining with the Bullus serum, indicating the presence of components of Adhesion Complexes. Adhesion Complexes are known to be involved in the adhesion of the corneal epithelial tissue to the underlying stroma and this result indicates that the corneal epithelial tissue anterior to the implant has analogous expression of these adhesion-promoting components.

These results show that the macroporous form of a material of this invention supports the initial attachment and outgrowth of corneal epithelial tissue to cover a corneal onlay implant. The material enables the development of a coverage of corneal epithelial tissue to occur within several days of the implantation. Furthermore, the material can support the development of a functional corneal epithelial tissue coverage, with the tissue coverage having an organised structure similar to the stratification that is seen in normal corneal epithelium as well as the expression, in the basal epithelial cell layer, of components of Adhesion Complex structures.

EXAMPLE 14 ("Z 1.4")

A further microporous form of the polymer of Example 8 was obtained by polymerizing the following mixture by the method of Example 11.

|  | Parts by weight |
|---|---|
| Macromonomer of Formula I (n = 1) | 85 |
| Isopropanol | 25 |
| Darocur 1173 (Ciba-Geigy) | 0.30 |

Using the method outlined in Example 11, the water content was determined to be 15% The permeability was:

|  | Permeability cm/s |
|---|---|
| Glucose | $1.3 \times 10^{-5}$ |
| Inulin | $0.4 \times 10^{-5}$ |
| Albumin | $9.0 \times 10^{-8}$ |

EXAMPLE 15

The polymers of Example 11, 12, 13 and 14 are coated with collagen using methods similar to those known to the art. The materials are then evaluated for their ability to support tissue outgrowth from corneal epithelial tissue buttons. The uncoated materials are also examined.

The ability of the materials to support the outgrowth of corneal epithelial tissue was determined by the methods described in Example 2. Table 6 shows that the materials support the outgrowth of corneal epithelial tissue to an equivalent extent to the polymer of example 8. Furthermore, the materials also supported outgrowth of corneal epithelial tissue when the polymer was precoated with a collagen coating.

TABLE 6

| Example | Polymer Name | Migration Index (± std dev) |
|---|---|---|
|  | TCPS | 7.3 (± 1.1) |
| Example 13 | Z 1.1 | 4.3 (± 0.6) |
|  | Z 1.1 + collagen | 4.5 (± 0.2) |
| Example 11 | Z 1.2 | 4.1 (± 0.2) |
|  | Z 1.2 + collagen | 5.7 (± 1.7) |
| Example 12 | Z 1.3 | 5.1 (± 0.7) |
|  | Z 1.3 + collagen | 6.0 (± 0.0) |
| Example 14 | Z 1.4 | 5.2 (± 0.9) |
|  | Z 1.4 + collagen | 7.8 (± 0.4) |
| Example 8 | Z 1.0 | 4.1 (± 0.6) |

Example 16

This example illustrates the preparation of a macromonomer of formula I (n=1.0), where Q is the residue derived from methacryloyl chloride, x is 10 and y is 14. The hydroxyl terminated PFPE (n=1.0), 107 g, was placed in a separation funnel and washed with 20 ml of petroleum spirits. The PFPE fraction was transferred to a round bottom flask fitted with a magnetic stirrer bar and dried overnight under vacuum (0.1 mm Hg) at 105° C.

On cooling, the 20.02 g (9.9 mMol) of the PFPE was placed in a 3-neck round bottom flask furnished with a magnetic stirrer bar, dropping funnel, nitrogen inlet and gas bubbler. The PFPE was diluted with 3.06 g (30.1 mMol) of triethylamine (Aldrich) and 20 ml trichlorotrifluoroethane (TCTFE) while 3.06 g (29.3 mMol) of methacryloyl chloride (Aldrich) was diluted with 20 ml of TCTFE then placed in the dropping funnel. The methacryloyl chloride was slowly added dropwise to the PFPE mixture with stirring at room temperature. Once the addition was complete the reaction was allowed to proceed overnight at room temperature under an atmosphere of nitrogen.

The triethylamine hydrochloride salt was filtered off. The solution containing the macromonomer was placed in a separating funnel and washed with 30 ml of water then dried over magnesium sulfate. The dried solution was filtered and the solvent was removed under reduced pressure to yield the PFPE dimethacrylate as a clear, faintly yellow colored oil. The solution was stored in the freezer and filtered prior to use.

Example 17

The following composition is placed in polypropylene flat molds (0.2 mm thick) and polymerized for three hours under irradiation from 365 nm UV lamps:

|  | Parts by weight |
|---|---|
| Macromonomer from Example 16 | 32 |
| Isopropyl acetate | 8 |
| EGDMA (Ethylene glycol dimethacrylate) | 0.7 |
| Darocur 1173 (Ciba-Geigy) | 0.1 |

After demoulding, the resulting flat discs were extracted using the procedure of Example 3. The polymer discs were then evaluated for bovine corneal epithelial cell attachment, according to the procedure of Example 2, and showed a similar cell density and morphology to the polymer of Example 3, when examined under identical conditions. This shows that the polymer supports cell growth.

Those skilled in the art will appreciate that the invention described herein is susceptible to variations and modifications other than those specifically described. It is to be understood that the invention includes all such variations and modifications which fall within the its spirit and scope. The invention also includes all of the steps, features, compositions and compounds referred to or indicated in this specification, individually or collectively, and any and all combinations of any two or more of said steps or features.

We claim:

1. An ocular prosthesis formed from a cell growth substrate polymer comprising a macromonomer of the formula I:

Q-(PFPE-L)n-1-PFPE-Q (I)

wherein n is at least 1.0;
each PFPE may be the same or different and is a perfluorinated polyether of formula 11:

—OCH₂CF₂O(CF₂CF₂O)ₓ(CF₂O)ᵧCF₂CH₂O— (II)

wherein the CF₂CF₂O and CF₂O units may be randomly distributed or distributed as blocks throughout the chain and wherein x and y may be the same or different such that the molecular weight of the perfluoropolyether is in the range of from 242 to 4000,
L is a difunctional linking group; and Q at each end of the macromonomer is the same or different and is a polymerizable group, wherein said ocular prothesis is a corneal implant for use in surgical implantation into or onto the cornea of a mammal wherein said implant has an optical axis region with optical characteristics which provide visual acuity therethrough and a porosity sufficient to allow passage therethrough of tissue fluid components having a molecular weight greater than 10,000 daltons, thereby providing for a flux of tissue fluid between cells anterior of the implant and cells posterior thereof, wherein the porosity of the optical axis region is such that it allows the flux of tissue fluid components whilst excluding ingrowth of ocular tissue.

2. A cornea implant according to claim 1 wherein the implant is coated with one or more components which promote the growth of tissue adjacent to the implant and/or cell adhesion to the implant.

3. A corneal implant according to claim 1 wherein porosity of the implant is provided by a plurality of pores having a size sufficient to allow passage through the implant of proteinaceous tissue fluid components having a molecular weight greater than 10,000 daltons but which excludes tissue ingrowth.

4. A corneal implant according to claim 3 wherein said plurality of pores comprise a diameter between 15 nanometres and 0.5 micrometres.

5. A method for using a polymer of the formula I for the manufacture of a cell growth material or implant, comprising the step of producing a cell growth or implant substrate from said polymer, wherein said formula I is:

Q-(PFPE-L)ₙ-1-PFPE-Q (I)

wherein n is at least 1.0;
each PFPE may be the same or different and is a perfluorinated polyether of formula II:

—OCH₂CF₂O(CF₂CF₂O)ₓ(CF₂O)ᵧCF₂CH₂O— (II)

wherein the CF₂CF₂O and CF₂O units may be randomly distributed or distributed as blocks throughout the chain and wherein x and y may be the same or different such that the molecular weight of the perfluoropolyether is in the range of from 242 to 4000,
L is a difunctional linking group; and
Q at each end of the macromonomer is the same or different and is a polymerizable group.

6. A medical implant formed from or comprising a cell growth substrate polymer of the formula I:

Q-(PFPE-L)n-1-PFPE-Q (I)

wherein n is at least 1.0;
each PFPE may be the same or different and is a perfluorinated polyether of formula 11:

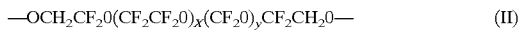
—OCH₂CF₂O(CF₂CF₂O)ₓ(CF₂O)ᵧCF₂CH₂O— (II)

wherein the CF₂CF₂O and CF₂O units may be randomly distributed or distributed as blocks throughout the chain and wherein x and y may be the same or different such that the molecular weight of the perfluoropolyether is in the range of from 242 to 4000,
L is a difunctional linking group; and
Q at each end of the macromonomer is the same or different and is a polymerizable group.

7. A tissue culture apparatus formed from or comprising a cell growth substrate polymer of the formula I:

$$Q\text{-(PFPE-L)}_n\text{-1-PFPE-Q} \qquad (I)$$

wherein n is at least 1.0;

each PFPE may be the same or different and is a perfluorinated polyether of formula 11:

$$-OCH_2CF_2O(CF_2CF_2O)_x(CF_2O)_yCF_2CH_2O- \qquad (II)$$

wherein the $CF_2CF_2O$ and $CF_2O$ units may be randomly distributed or distributed as blocks throughout the chain and wherein x and y may be the same or different such that the molecular weight of the perfluoropolyether is in the range of from 242 to 4000, L is a difunctional linking group; and Q at each end of the macromonomer is the same or different and is a polymerizable group.

8. A biological reactor formed from or comprising a cell growth substrate polymer of the formula I:

$$Q\text{-(PFPE-L)}_n\text{-1-PFPE-Q} \qquad (I)$$

wherein n is at least 1.0;

each PFPE may be the same or different and is a perfluorinated polyether of formula 11:

$$-OCH_2CF_2O(CF_2CF_2O)_x(CF_2O)_yCF_2CH_2O- \qquad (II)$$

wherein the $CF_2CF_2O$ and $CF_2O$ units may be randomly distributed or distributed as blocks throughout the chain and wherein x and y may be the same or different such that the molecular weight of the perfluoropolyether is in the range of from 242 to 4000, L is a difunctional linking group; and Q at each end of the macromonomer is the same or different and is a polymerizable group.

9. An optical instrument formed from or comprising a cell growth substrate polymer of the formula I:

$$Q\text{-(PFPE-L)}_n\text{-1-PFPE-Q} \qquad (I)$$

wherein n is at least 1.0;

each PFPE may be the same or different and is a perfluorinated polyether of formula 11:

$$-OCH_2CF_2O(CF_2CF_2O)_x(CF_2O)_yCF_2CH_2O- \qquad (II)$$

wherein the $CF_2CF_2O$ and $CF_2O$ units may be randomly distributed or distributed as blocks throughout the chain and wherein x and y may be the same or different such that the molecular weight of the perfluoropolyether is in the range of from 242 to 4000, L is a difunctional linking group; and Q at each end of the macromonomer is the same or different and is a polymerizable group.

10. A microscope slide formed from or comprising a cell growth substrate polymer of the formula I:

$$Q\text{-(PFPE-L)}_n\text{-1-PFPE-Q} \qquad (I)$$

wherein n is at least 1.0;

each PFPE may be the same or different and is a perfluorinated polyether of formula 11:

$$-OCH_2CF_2O(CF_2CF_2O)_x(CF_2O)_yCF_2CH_2O- \qquad (II)$$

wherein the $CF_2CF_2O$ and $CF_2O$ units may be randomly distributed or distributed as blocks throughout the chain and wherein x and y may be the same or different such that the molecular weight of the perfluoropolyether is in the range of from 242 to 4000, L is a difunctional linking group; and Q at each end of the macromonomer is the same or different and is a polymerizable group.

11. The method of claim 5 wherein n is between 1 and 5.

12. The method of claim 5 wherein n is between 2 and 4.

13. The method of claim 5 wherein Q is a polymerizable group which comprises an ethylenically unsaturated moiety.

14. The method of claim 5 wherein Q is selected from the group consisting of acryloyl, methacryloyl, styryl, acrylamido, acrylamidoalkyl, urethanemethacrylate, or any substituted derivatives thereof.

15. The method of claim 5 wherein L is a bivalent residue (—C(O)—NH—R—NH—C(O)—) of a diisocyanate.

16. The method of claim 5 wherein the bivalent residue is derived from a diisocyanate selected from the group consisting of trimethylhexamethylene-diisocyanate (TMHMDI), isophorone diisocyanate (IPDI), methylenediphenyl diisocyanate (MDI) and 1,6-hexamethylenediisocyanate (HMDI).

17. The method of claim 5 wherein x is in the range of from 0 to 20.

18. The method of claim 5, wherein x is in the range of from 8 to 12.

19. The method of claim 5 wherein y is in the range from 0 to 25.

20. The method of claim 5 wherein y is in the range of from 10 to 14.

21. The method of claim 5 wherein n is in the range of from 2 to 5, L is the bivalent residue derived from trimethylhexamethylene diisocyanate (TMHMDI) and Q is the residue derived from isocyanatoethyl methacrylate.

22. The method of claim 5 wherein the macromonomer of the formula III:

$CH_2=C(CH_3)COOC_2H_4NHCO—(—PFPE—CONH—R—NHCO—)_{n-1}—PFPE—CONHC_2H40COC(CH3)=CH_2$ wherein PFPE is a perfluorinated polyether of formula II $$-OCH_2CF_2O(CF_2CF_2O)_x(CF_2O)_yCF_2CH_2O- \qquad (II)$$

wherein the $CF_2CF_2O$ and $CF_2O$ units may be randomly distributed or distributed as blocks throughout the chain, n is at least 1.0, R is the trimethylhexamethylene component of TMHMDI, and wherein x is in the range of from 8 to 10 and y is in the range of from 10 to 14.

23. The method of claim 5 wherein said polymer substrate further comprising an adsorbed or coupled adhesive glycoprotein.

24. The method of claim 5 wherein said adhesive glycoprotein is selected from the group consisting of fibronectin, vitronectin, collagen, laminin and thrombosponden.

* * * * *